(12) United States Patent
Church et al.

(10) Patent No.: US 10,774,366 B2
(45) Date of Patent: Sep. 15, 2020

(54) METHOD OF MAKING POLYNUCLEOTIDES USING CLOSED-LOOP VERIFICATION

(71) Applicant: President and Fellows of Harvard College, Cambridge, MA (US)

(72) Inventors: George M. Church, Brookline, MA (US); Kettner John Frederick Griswold, Jr., Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/083,714

(22) PCT Filed: Mar. 9, 2017

(86) PCT No.: PCT/US2017/021498
§ 371 (c)(1),
(2) Date: Sep. 10, 2018

(87) PCT Pub. No.: WO2017/156218
PCT Pub. Date: Sep. 14, 2017

(65) Prior Publication Data
US 2019/0062804 A1  Feb. 28, 2019

Related U.S. Application Data

(60) Provisional application No. 62/306,665, filed on Mar. 11, 2016.

(51) Int. Cl.
*C12Q 1/68* (2018.01)
*C12Q 1/6806* (2018.01)
*C12P 19/34* (2006.01)
*C40B 40/06* (2006.01)

(52) U.S. Cl.
CPC ............ *C12Q 1/6806* (2013.01); *C12P 19/34* (2013.01); *C40B 40/06* (2013.01)

(58) Field of Classification Search
CPC .................................................. C12Q 1/6806
USPC ........................................................... 435/6.1
See application file for complete search history.

(56) References Cited

U.S. PATENT DOCUMENTS

| | | |
|---|---|---|
| 5,872,244 A | 2/1999 | Hiatt et al. |
| 9,279,149 B2 | 3/2016 | Efcavitch et al. |
| 2010/0099080 A1 | 4/2010 | Church et al. |
| 2013/0085073 A1 | 4/2013 | Meuleman et al. |
| 2013/0178374 A1* | 7/2013 | Eckhardt ............ C12N 15/1089 506/5 |
| 2019/0040459 A1 | 2/2019 | Efcavitch et al. |

* cited by examiner

*Primary Examiner* — Jezia Riley
(74) *Attorney, Agent, or Firm* — Banner & Witcoff, Ltd.

(57) ABSTRACT

A method for making a polynucleotide is provided including (a) delivering one or more reaction reagents including an error prone or template independent DNA polymerase, cations and a selected nucleotide to a reaction site including an initiator sequence having a terminal nucleotide for a time period and under conditions capable of covalently adding one or more of the selected nucleotide to the terminal nucleotide at the 3' end of the initiator such that the selected nucleotide becomes a terminal nucleotide, and (b) determining whether the selected nucleotide has been added to the terminal nucleotide, wherein if the selected nucleotide has not been added to the terminal nucleotide, then repeating step (a) until the selected nucleotide has been added, and (c) repeating steps (a) and (b) until the polynucleotide is formed.

12 Claims, 2 Drawing Sheets

METHOD OF MAKING POLYNUCLEOTIDES USING CLOSED-LOOP VERIFICATION

RELATED APPLICATIONS

This application is a National Stage Application under 35 U.S.C. 371 of co-pending PCT application PCT/US17/21498 designating the United States and filed Mar. 9, 2017; which claims the benefit of U.S. provisional application No. 62/306,665 and filed Mar. 11, 2016 each of which are hereby incorporated by reference in their entireties.

FIELD

The present invention relates in general to methods of making oligonucleotides and polynucleotides using enzymatic synthesis.

BACKGROUND

Methods of making polynucleotides are known. One method for large-scale de novo DNA synthesis includes use of automated instruments employing solid phase phosphoramidite chemistry first developed by Beaucage and Caruthers. This chemistry is widely practiced in a 3-4 step process on solid support, involving iterative pH-mediated deprotection and coupling in organic solvents. Typically, this automated process synthesizes up to 384 oligos simultaneously at scales up to 100 nmol. Length limitations and error rates of this process exist due to exponentially decaying full length oligo fractions due to compounding sub-unity stepwise yields and destructive side reactions, such as acidic depurination.

SUMMARY

The disclosure provides methods of making a polynucleotide using an error prone or template independent DNA polymerase, cations and selected nucleotides. An exemplary template independent DNA polymerase is terminal deoxynucleotidyl transferase (TdT) which is used to synthesize single strand DNA by incorporation of nucleotides at the end of 3' end of a initiator strand or growing oligonucleotide or polynucleotide. The disclosure provides use of closed-loop verification of nucleotide addition.

The disclosure provides a method for making a polynucleotide including the steps of (a) delivering one or more reaction reagents including an error prone or template independent DNA polymerase, cations and a selected nucleotide to a reaction site including an initiator sequence having a terminal nucleotide for a time period and under conditions capable of covalently adding one or more of the selected nucleotide to the terminal nucleotide at the 3' end of the initiator such that the selected nucleotide becomes a terminal nucleotide, and (b) determining whether the selected nucleotide has been added to the terminal nucleotide, wherein if the selected nucleotide has not been added to the terminal nucleotide, then repeating step (a) until the selected nucleotide has been added, and (c) repeating steps (a) and (b) until the polynucleotide is formed. The disclosure provides that the selected nucleotide includes a labile protecting group. The disclosure provides that the selected nucleotide includes a photolabile protecting group. The disclosure provides that the selected nucleotide includes a chemically photolabile protecting group. The disclosure provides that the selected nucleotide includes an enzymatically labile protecting group. The disclosure provides that a single selected nucleotide is covalently added. The disclosure provides that the error prone template independent DNA polymerase is terminal deoxynucleotide transferase. The disclosure provides a plurality of reaction sites where steps (a) and (b) are performed. The disclosure provides that an incorrect nucleotide is added to the terminal nucleotide which is removed before repeating step (a) until the selected nucleotide has been added. The disclosure provides that whether the selected nucleotide has been added to the terminal nucleotide is determined by monitoring of a fluorescent signal. The disclosure provides that whether the selected nucleotide has been added to the terminal nucleotide is determined by monitoring photons, electrons, pH, or a chemical entity. The disclosure provides a plurality of reaction sites where steps (a) and (b) are performed and wherein the plurality of reaction sites are monitored simultaneously or in parallel to determine whether the selected nucleotide has been added to the terminal nucleotide or whether an incorrect nucleotide has been added to the terminal nucleotide. The disclosure provides a plurality of reaction sites where steps (a) and (b) are performed and wherein the plurality of reaction sites are monitored simultaneously or in parallel to determine whether the selected nucleotide has been added to the terminal nucleotide or whether an incorrect nucleotide has been added to the terminal nucleotide, and for one or more reaction sites where the selected nucleotide has not been added to the terminal nucleotide, repeating step (a) at each of the one or more reaction sites until the selected nucleotide has been added. The disclosure provides a plurality of reaction sites where steps (a) and (b) are performed and wherein the plurality of reaction sites are monitored simultaneously or in parallel to determine whether the selected nucleotide has been added to the terminal nucleotide or whether an incorrect nucleotide has been added to the terminal nucleotide, and for one or more reaction sites where the incorrect nucleotide has been added to the terminal nucleotide, removing the incorrect nucleotide and repeating step (a) at each of the one or more reaction sites until the selected nucleotide has been added. The disclosure provides that the reaction reagents are removed from the reaction site by a volume of wash fluid. The disclosure provides that the one or more reaction reagents are delivered by microfluidics. The disclosure provides that the selected nucleotide is a natural nucleotide or a nucleotide analog. The disclosure provides that the selected nucleotide includes a cleavable linker and a detectable moiety attached thereto.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which.

DETAILED DESCRIPTION

Figure 1:
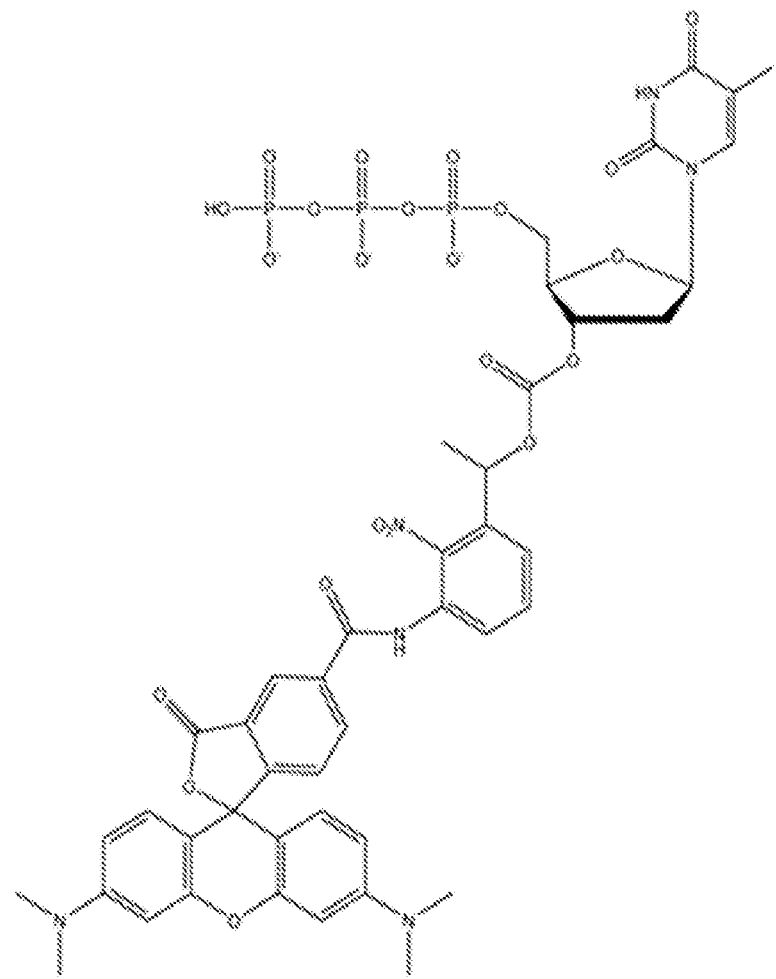
FIG. 1 depicts an exemplary dNTP with a cleavable protecting group and a fluorescent moiety.

The present disclosure is directed to the oligonucleotide sequences or polynucleotide sequences, whether random or designed, that are synthesized using enzymatic oligonucleotide synthesis reactions where an enzyme and a nucleotide (and related reagents or conditions) are placed at a desired site on a substrate under appropriate reaction conditions and the nucleotide is covalently bound to an existing nucleotide, such as an initiator sequence, which may be attached to a support. The oligonucleotide sequences may be synthesized using polymerases, such as error-prone polymerases under conditions where the reagents are localized at a location on a substrate for a period of time and under such conditions to maximize probability of adding a single nucleotide or desired number of nucleotides. The present disclosure provides that a closed-loop verification method is used to determine that a desired number of nucleotides have been covalently added. A suitable wash may also be used at a desired time to remove one or more reagents from the reaction site or location. The reagents or wash may be added to a location or reaction site using any suitable fluidics system or other systems known to those of skill in then art.

Polymerases, including without limitation error-prone template-dependent polymerases, modified or otherwise, can be used to create nucleotide polymers having a random or known or desired sequence of nucleotides. Template-independent polymerases, whether modified or otherwise, can be used to create the nucleic acids de novo. Ordinary nucleotides are used, such as A, T/U, C or G. The disclosure provides for the use of chain terminating moieties on nucleotides. Such nucleotides with chain terminating moieties may be referred to as reversible terminators. The disclosure also provides for the use of nucleotides which lack chain terminating moieties. A template independent polymerase may be used to make the nucleic acid sequence. Such template independent polymerase may be error-prone which may lead to the addition of more than one nucleotide resulting in a homopolymer. Sensors, such as light activated sensors, metabolic products or chemicals, that are activated by ligands can be used with such polymerases.

Oligonucleotide sequences or polynucleotide sequences are synthesized using an error prone polymerase, such as template independent error prone polymerase, and common or natural nucleic acids, which may be unmodified. Initiator sequences or primers are attached to a substrate, such as a silicon dioxide substrate, at various locations whether known, such as in an addressable array, or random. Methods and moieties for attaching nucleotide sequences to a substrate are well known in the art. Such moieties may be cleavable such that the resultant oligonucleotide may be cleaved from the substrate surface, for example, by chemical reagents or light. Reagents including at least a selected nucleotide, a template independent polymerase and other reagents required for enzymatic activity of the polymerase are applied at one or more locations of the substrate where the initiator sequences are located and under conditions where the polymerase adds one or more than one or a plurality of the nucleotide to the initiator sequence to extend the initiator sequence. The nucleotides ("dNTPs") may be applied or flow in periodic applications. Blocking groups or reversible terminators may be used with the dNTPs. Nucleotides with blocking groups or reversible terminators are known to those of skill in the art. According to an additional embodiment when reaction conditions permit, more than one dNTP may be added to form a homopolymer run when common or natural nucleotides are used with a template independent error prone polymerase. When blocking groups or reversible terminators are used, the blocking group or terminating group is removed which allows extension of the growing oligonucleotide by addition of the next nucleotide.

Polymerase activity may be modified using photo-chemical or electrochemical modulation as a reaction condition so as to minimize addition of dNTP beyond a single dNTP. A wash is then applied to the one or more locations to remove the reagents. The steps of applying the reagents and the wash are repeated until desired nucleic acids are created. The reagents may be added to one or more than one or a plurality of locations on the substrate in series or in parallel or the reagents may contact the entire surface of the support, such as by flowing the reagents across the surface of the support. Reaction conditions for adding a nucleotide using an enzyme are known to those of skill in the art and may be readily determined.

In addition, according to certain embodiments, polymerases can be modulated to be light sensitive for light based methods. According to this aspect, light is modulated to tune the polymerase to add a nucleotide or a number of nucleotides. The light is shone on individual locations or pixels of the substrate where the polymerase, the nucleotide and appropriate reagents and reaction conditions are present. In this manner, a nucleotide is added to an initiator sequence or an existing nucleotide as the polymerase is activated by the light.

A flow cell or other channel, such a microfluidic channel or microfluidic channels having an input and an output is used to deliver fluids including reagents, such as a polymerase, a nucleotide and other appropriate reagents and washes to particular locations on a substrate within the flow cell, such as within a reaction chamber. A desired location, such as a grid point on a substrate or array, can be provided with reaction conditions to facilitate covalent binding of a nucleotide to an initiator sequence, an existing nucleotide or an existing oligonucleotide. Certain reaction conditions can be provided at the reactive site to prevent further attachment of an additional nucleotide at the same location. Then, reaction conditions to facilitate covalent binding of a nucleotide to an existing nucleotide can be provided to the same location in a method of making an oligonucleotide at that desired location. One of skill will recognize that reaction conditions will be based on dimensions of the substrate reaction region, reagents, concentrations, reaction temperature, and the structures used to create and deliver the reagents and washes. According to certain aspects, pH and other reactants and reaction conditions can be optimized for the use of TdT to add a dNTP to an existing nucleotide or oligonucleotide in a template independent manner. For example, Ashley et al., Virology 77, 367-375 (1977) hereby incorporated by reference in its entirety identifies certain reagents and reaction conditions for dNTP addition, such as initiator size, divalent cation and pH. TdT was reported to be active over a wide pH range with an optimal pH of 6.85. Methods of providing or delivering dNTP, rNTP or rNDP are useful in making nucleic acids. Release of a lipase or other membrane-lytic enzyme from pH-sensitive viral particles inside dNTP filled-liposomes is described in *J Clin Microbiol.* May 1988; 26(5): 804-807. Photo-caged rNTPs or dNTPs from which NTPs can be released, typically nitrobenzyl derivatives sensitive to 350 nm light, are commercially available from Lifetechnologies. Rhoposin or bacterio-opsin triggered signal transduction resulting in vesicular or other secretion of nucleotides is known in the art. With these methods for delivering dNTPs, the nucleotides should be removed or sequestered between the first primer-polymerase encountered and any downstream.

Figure 2:
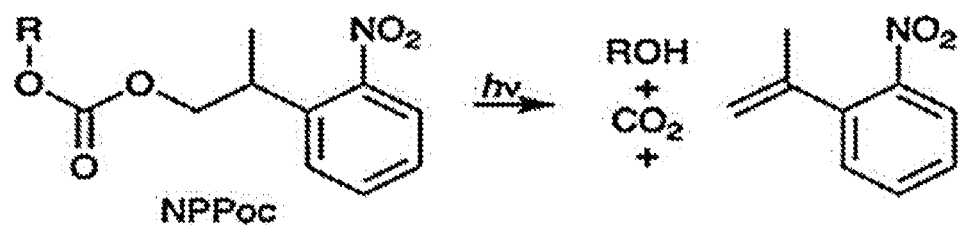
FIG. 2 depicts using light to cleave a photolabile protecting group.

The disclosure provides use of reversible terminator chemistry in the synthesis of nucleic acids using enzymes, such as a template independent polymerase, which enzymatically adds Deoxynucleotide Triphosphates (dNTPs) to the 3' OH terminus of ssDNA primer in the absence of a template sequence. The identity of each nucleotide incorporation is dependent on the environmental context at the Enzyme-ssDNA complex. The environmental context can be modulated such that a desired ssDNA sequence is synthesized. One example of a Template independent DNA polymerase is Terminal deoxynucleotidyl Transferase (TdT). Reversible terminators are dNTP analogs that are modified to inhibit subsequent enzymatic extension by DNA polymerases, and contain labels that produce a signal reporting the identity of the incorporated nucleotide. The extension inhibiting component and the label component of the nucleotide molecule are designed to be removed under mild conditions (deprotection), such that the extended DNA substrate can be extended further without damage to the DNA. The disclosure provides for the use of a reversible terminator that contains a photolabile terminator that is covalently attached to a fluorophore. This particular reversible terminator chemistry facilitates deterministic tracking of the coupling and deprotection steps of the DNA molecule throughout the synthesis process. An exemplary protecting group for use in reversible terminator chemistry is a photolabile (nitrophenyl)propyl carbonyl ester (NPPOC), that cleaves under UV light from roughly 350 nm to 405 nanometers. See Klan, P. et al. Photoremovable protecting groups in chemistry and biology: reaction mechanisms and efficacy. *Chem. Rev.* 113, 119-91 (2013) hereby incorporated by reference in its entirety. To maintain compatibility with the active monitoring scheme, the phenyl ring may be modified to contain a fluorophore linked at the ortho, meta or para position. An exemplary position is the 3' position. An exemplary flourophore labeled 3'-O—NPPOC protected dTTP is provided in FIG. 1. Exemplary deprotection chemistry is illustrated in FIG. 2.

The disclosure provides for attaching a fluorescent label to the benzyl ring of a 3' O nitrobenzyl carbonate ester of a nucleotide triphosphate. The fluorophore can also be located to the ortho or para position. In an alternative embodiment, a flexible linker such as a flexible polymer linker such as a flexible PEG linker can be added between fluorophore and the benzyl ring. Flexible linkers are known to those of skill in the art. Four different fluorophores can be chosen that also fluoresce under wavelengths which do not cleave the nitrobenzyl carbonate ester. An example is TAMRA-NPPOC-dTTP derivatives.

Figure 3:
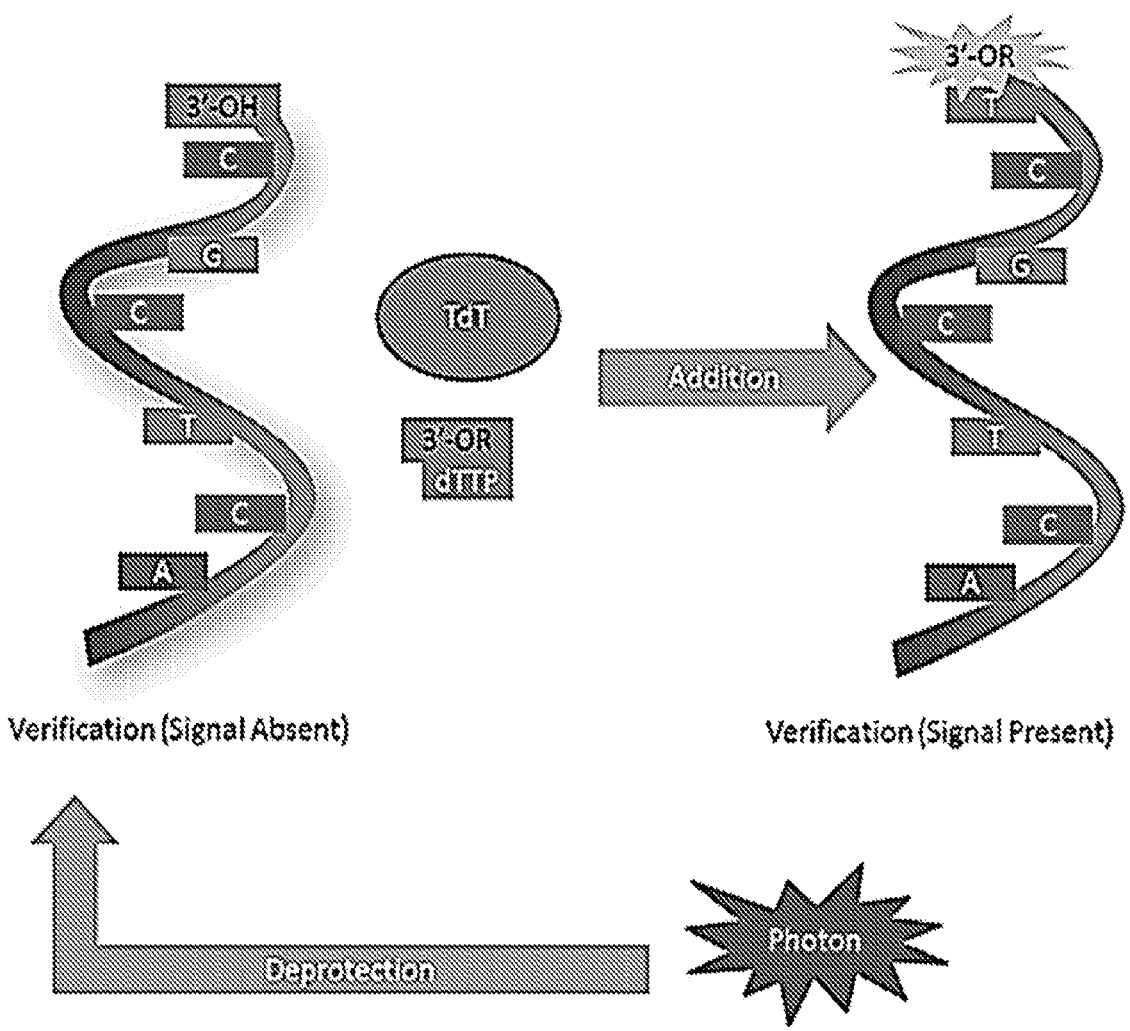
FIG. 3 depicts a process or extending a growing nucleic using a photolabile protecting group and a fluorescent moiety.

The disclosure provides that dilute DNA primers with 5' biotin moieties are first immobilized to the center of a reaction well. For each nucleotide addition, a 3'-OH protected dNTP is flowed in with TdT. For each photodeprotected primer there will be a single incorporation event, halted by the displayed terminator on the 3'-OH. Following washing, incorporation of the nucleotide is verified by the appearance of the corresponding fluorescent signal. Next, a pulsed laser is used to deprotect the molecules. Deprotection is verified by monitoring for the disappearance of said terminal fluorescent signal. Once deprotection is verified, the process is repeated for each nucleotide in the desired sequence. An exemplary process is illustrated in FIG. 3. The disclosure provides for an array synthesis method in which 3'-OH protected dNTPs are flowed in a repeated cycle, such as from [d]A→T→C→G. Multiplex synthesis across reaction wells in the array may be accomplished by spatially modulated photodeprotection. For example, the device can be controlled by a Spatial Light Modulator (SLM), Digital micromirror array or Liquid Crystal on Silicon (LCOS) modulators.

The disclosure provides for the use of a method for verifying or detecting whether a nucleotide has been added to the nucleic acid or initiator bound to the substrate. The disclosure provides for verifying or detecting whether the enzymatic method has been successful at single nucleotide extension of the nucleic acid or initiator sequence bound to the substrate. Verification of nucleotide incorporation and identity includes monitoring a signal at all transitions, i.e., extension steps, required in the extension process, to determine if the DNA extension process does or does not complete a transition. The verification process can take place at one or more or a plurality of synthesis locations or sites on a substrate, individually or in parallel or simultaeously.

The disclosure provides that each step in extension can be verified at every transition for a single molecule. This may be referred to as single molecule extension verification which leads to high fidelity DNA synthesis. A single molecule on the substrate is monitored to verify addition of the nucleotide. A plurality of single molecules at different synthesis sites on the substrate is monitored to verify addition of the nucleotide at that particular site. If a failed extension is detected or otherwise determined for a single molecule on the substrate, then the extension step can be repeated one or more times until the extension is successful in that single molecule. Such an approach is termed a "closed-loop" approach as the extension step for a single molecule is repeated until the correct nucleotide has been added. The "closed-loop" methods described herein produce a DNA molecule with perfect fidelity up to the signal fidelity limit. The repeated step can be made anywhere where the influence of the process is orthogonal to other DNA molecules. For example, the verification step can be carried out at one or more synthesis locations on the substrate while not being carried out at one or more other synthesis locations on the substrate. The modulation scheme can be chosen such that the mutual orthogonality constraint is always satisfied for every molecule at every step. The disclosure provides that verification signals can be photons, electrons, changes in pH, molecular byproducts, and the like, that report successful nucleotide incorporation events.

The disclosure provides that verification of proper nucleotide addition with the described reversible terminator is accomplished by appearance of a fluorescent signal after the excess reagent has been washed away, and verification of deprotection is accomplished by registering the disappearance of signal after cleavage of the protecting group, and washing excess reagent away. The disclosure provides that single molecule closed-loop extension is advantageous because the signal does not dephase and the fidelity of the synthesis is governed by the fidelity of the signal readout method.

The disclosure provides that a nucleotide releases or otherwise provides or generates a signal upon incorporation, or a signal is generated upon incorporation, such as fluorescence. The absence of the signal following a nucleotide incorporation attempt indicates a potential indel error. In this context, the incorporation can be reattempted until a positive signal is received. If a state of the primer needs to be altered subsequent to further primer extension, then the completion of deprotection can be monitored by the absence of prior incorporation signal. For example, if a protecting group that blocks further enzymatic extension of a primer contains a fluorescent molecule, then absence of the fluorescent signal verifies successful deprotection. The deprotection of the molecule can be reattempted until the signal is no longer observed.

Depending on the extension modulation scheme used, a signal uniquely reporting the identity of the incorporated nucleotide can be monitored to identify nucleotide misincorporation events. Misincorporations can include introduction of the improper nucleotide, or more than one incorporation event per extension cycle. Misincorporations can occur due to improperly deprotected primers at any extension process. In one embodiment, the signal is a fluorescent signal, produced by a cleavable fluorophore that functions as an extension terminator group on the nucleotide. If an unexpected signal introduced by misincorporation appears during any DNA extension cycle, then an error correction procedure must be followed to excise the misincorporation and possibly from the 3' end of the DNA strand. Methods of removing an added nucleotide from a nucleic acid are known to those of skill in the art. An exemplary method of correcting the addition of an incorrect nucleotide includes tailing with deoxyuridine triphosphate (dUTP) followed by annealing with an oligomer, such as a heptamer, to produce a double stranded structure which can be recognized by a "chewing" enzyme such as uracil glycosylase (UDG) and/or Mutant(D70A/E96A)APE1-FokI fusion. The disclosure provides removing unincorporated dUTP and the annealing oligomer before using a "chewing" enzyme such as uracil glycosylase (UDG) and/or Mutant(D70A/E96A)APE1-FokI fusion. The UDG cleaves out uracil and the Mutant(D70A/E96A)APE1-FokI fusion recognizes an AP site and generates either 2 bp or 3 bp nicks 5' to the 3' terminal nucleotide of the polynucleotide sequence. The process may be a self-limiting process and may be interated as desired to remove all misincorporated nucleotides. Other methods of removing a terminal nucleotide from a nucleic acid, enzymatic or otherwise, are known to those of skill in the art.

Terms and symbols of nucleic acid chemistry, biochemistry, genetics, and molecular biology used herein follow those of standard treatises and texts in the field, e.g., Komberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

Nucleic Acids and Nucleotides

As used herein, the terms "nucleic acid molecule," "nucleic acid sequence," "nucleic acid fragment" and "oligomer" are used interchangeably and are intended to include, but are not limited to, a polymeric form of nucleotides that may have various lengths, including either deoxyribonucleotides or ribonucleotides, or analogs thereof.

In general, the terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides (DNA) or ribonucleotides (RNA), or analogs thereof. A oligonucleotide is typically composed of a specific sequence of four nucleotide bases: adenine (A); cytosine (C); guanine (G); and thymine (T) (uracil (U) for thymine (T) when the polynucleotide is RNA). According to certain aspects, deoxynucleotides (dNTPs, such as dATP, dCTP, dGTP, dTTP) may be used. According to certain aspects, ribonucleotide triphosphates (rNTPs) may be used. According to certain aspects, ribonucleotide diphosphates (rNDPs) may be used.

The term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides. The present disclosure contemplates any deoxyribonucleotide or ribonucleotide and chemical variants thereof, such as methylated, hydroxymethylated or glycosylated forms of the bases, and the like. According to certain aspects, natural nucleotides are used in the methods of making the nucleic acids. Natural nucleotides lack chain terminating moieties. According to another aspect, the methods of making the nucleic acids described herein do not use terminating nucleic acids or otherwise lack terminating nucleic acids, such as reversible terminators known to those of skill in the art. The methods are performed in the absence of chain terminating nucleic acids or wherein the nucleic acids are other than chain terminating nucleic acids.

Examples of modified nucleotides include, but are not limited to diaminopurine, S2T, 5-fluorouracil, 5-bromouracil, 5-chlorouracil, 5-iodouracil, hypoxanthine, xantine, 4-acetylcyto sine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A (2012) KlenTaq polymerase replicates unnatural base pairs by inducing a Watson-Crick geometry, Nature Chem. Biol. 8:612-614; See Y J, Malyshev D A, Lavergne T, Ordoukhanian P, Romesberg F E. J Am Chem Soc. 2011 Dec. 14; 133(49):19878-88, Site-specific labeling of DNA and RNA using an efficiently replicated and transcribed class of unnatural base pairs; Switzer C Y, Moroney S E, Benner S A. (1993) Biochemistry. 32(39):10489-96. Enzymatic recognition of the base pair between isocytidine and isoguanosine; Yamashige R, Kimoto M, Takezawa Y, Sato A, Mitsui T, Yokoyama S, Hirao I. Nucleic Acids Res. 2012 March; 40(6):2793-806. Highly specific unnatural base pair systems as a third base pair for PCR amplification; and Yang Z, Chen F, Alvarado J B, Benner S A. J Am Chem Soc. 2011 Sep. 28; 133(38):15105-12, Amplification, mutation, and sequencing of a six-letter synthetic genetic system. Other non-standard nucleotides may be used such as dexfribed in Malyshev, D. A., et al., Nature, vol. 509, pp. 385-388 (15 May 2014) hereby incorporated by reference in its entirety.

Protecting Groups

The disclosure provides cleavable protecting groups or linkers known to those of skill in the art which are useful in the methods described herein. Exemplary protecting groups or linkers may be attached to the nucleobase or the 3' carbon to terminate enzymatic polynucleotide extension. Exemplary protecting groups or linkers may have a detectable moiety attached thereto. Exemplary cleavable protecting groups or linkers are described in Leriche, G., Chisholm, L., & Wagner, A. (2012). Cleavable linkers in chemical biology. *Bioorganic and Medicinal Chemistry*, 20(2), 571-582 hereby incorporated by reference in its entirety. It is to be understood that cleavable protecting groups are known to those of skill in the art and can be readily identify by literature search.

Detectable Moieties

The disclosure provides the following examples of detectable moieties that can be attached to a cleavable protecting group useful in the method described herein: Methoxycoumarin, Dansyl, Pyrene, Alexa Fluor 350, AMCA, Marina Blue dye, Dapoxyl dye, Dialkylaminocoumarin, Bimane, Hydroxycoumarin, Cascade Blue dye, Pacific Orange dye, Alexa Fluor 405, Cascade Yellow dye, Pacific Blue dye, PyMPO, Alexa Fluor 430, NBD, QSY 35, Fluorescein, Alexa Fluor 488, Oregon Green 488, BODIPY 493/503, Rhodamine Green dye, BODIPY FL, 2',7'-Dichloro-, fluorescein, Oregon Green 514, Alexa Fluor 514, 4',5'-Dichloro-, 2',7'-dimethoxy-, fluorescein (JOE), Eosin, Rhodamine 6G, BODIPY R6G, Alexa Fluor 532, BODIPY 530/550, BODIPY TMR, Alexa Fluor 555, Tetramethyl-, rhodamine (TMR), Alexa Fluor 546, BODIPY 558/568, QSY 7, QSY 9, BODIPY 564/570, Lissamine rhodamine B, Rhodamine Red dye, BODIPY 576/589, Alexa Fluor 568, X-rhodamine, BODIPY 581/591, BODIPY TR, Alexa Fluor 594, Texas Red dye, Naphthofluorescein, Alexa Fluor 610, BODIPY 630/650, Malachite green, Alexa Fluor 633, Alexa Fluor 635, BODIPY 650/665, Alexa Fluor 647, QSY 21, Alexa Fluor 660, Alexa Fluor 680, Alexa Fluor 700, Alexa Fluor 750, and Alexa Fluor 790 and the like. It is to be understood that detectable moieties are known to those of skill in the art and can be readily identify by literature search.

Exemplary Nucleotides with Cleavable Groups and Detectable Moieties

The disclosure provides certain exemplary nucleotides with cleavable groups or moieties and detectable groups or moieties. In general, the nucleotides have the structure below:

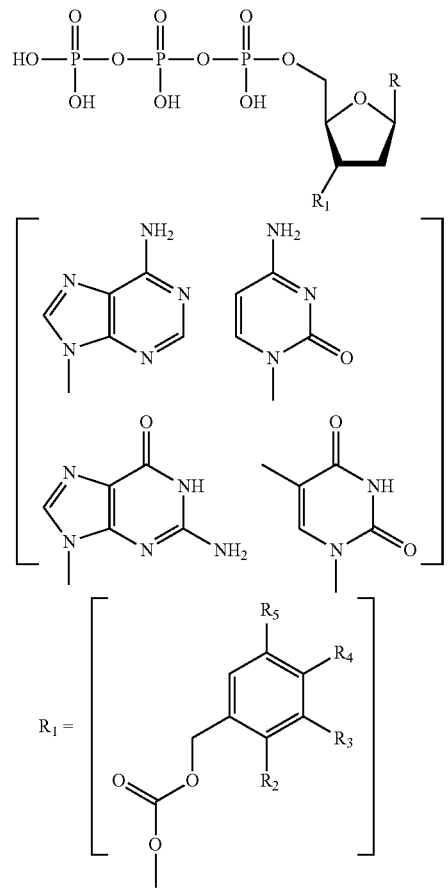

R represents standard base units and $R_1$ represents a cleavable linker, group or moiety. The disclosure provides that with respect to $R_1$, $R_2$ is $NO_2$; $R_3$ is a $R_7$ species as shown below or H; $R_4$ is H or $R_7$ and $R_5$ is H or an $R_6$ species as shown below.

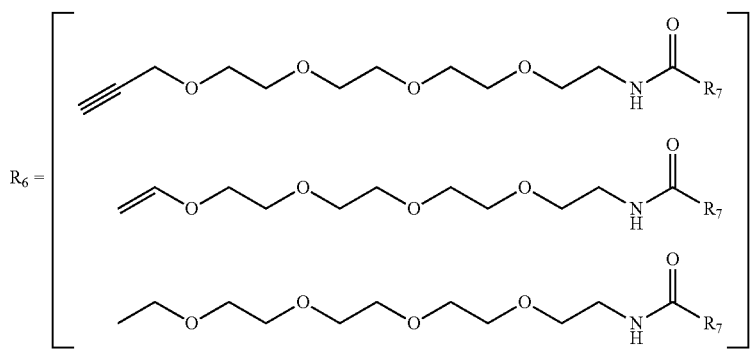

$R_7 =$ [ Methoxycoumarin, Dansyl, Pyrene, Alexa Fluor 350, AMCA, Marina Blue dye, Dapoxyl dye, Dialkylaminocoumarin, Bimane, Hydroxycoumarin, Cascade Blue dye, Pacific Orange dye, Alexa Fluor 405, Cascade Yellow dye, Pacific Blue dye, PyMPO, Alexa Fluor 430, NBD, QSY 35, Fluoresccin, Alexa Fluor 488, Oregon Green 488, BODIPY 493/503, Rhodamine Green dye, BODIPY FL, 2′,7′-Dichloro-, fluorescein, Oregon Green 514, Alexa Fluor 514, 4′,5′-Dichloro-, 2′,7′-dimethoxy-, fluorescein (JOE), Eosin, Rhodamine 6G, BODIPY R6G, Alexa Fluor 532, BODIPY 530/550, BODIPY TMR, Alexa Fluor 555, Tetramethyl-, rhodamine (TMR), Alexa Fluor 546, BODIPY 558/568, QSY 7, QSY 9, BODIPY 564/570, Lissamine rhodamine B, Rhodamine Red dye, BODIPY 576/589, Alexa Fluor 568, X-rhodamine, BODIPY 581/591, BODIPY TR, Alexa Fluor 594, Texas Red dye, Naphthofluorescein, Alexa Fluor 610, BODIPY 630/650, Malachite green, Alexa Fluor 633, Alexa Fluor 635, BODIPY 650/665, Alexa Fluor 647, QSY 21, Alexa Fluor 660, Alexa Fluor 680, Alexa Fluor 700, Alexa Fluor 750, and Alexa Fluor 790.

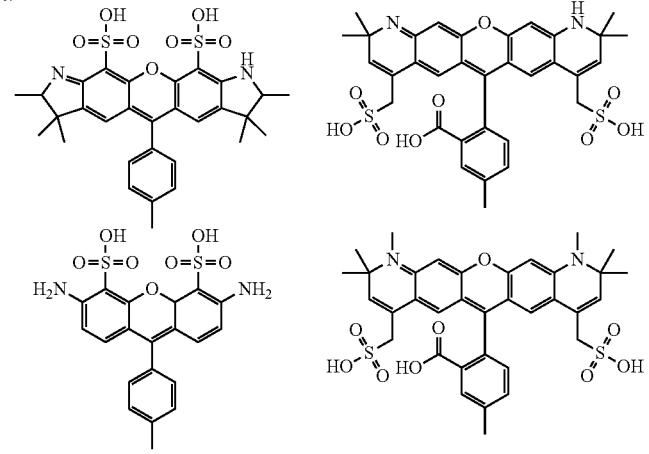

]

Exemplary compounds may be made by methods and techniques known to those of skill in the art. An exemplary method includes triphosgene nitrobenzyl chloride coupling to the protected nucleotide, sonagashira coupling (or heck coupling) [or Suzuki-Miyaura Coupling] of Amino-alkyne (or alkene) [or Mida Boronate Ester] PEG linker to the nitrobenzyl chloride, followed by detritylation, followed by deprotection of the nucleobase, followed by 5' Regioselective Phosphitylation, followed by N-Hydroxysuccinimide fluorophore to amine Peg Linker.

Exemplary compounds include the following structures.

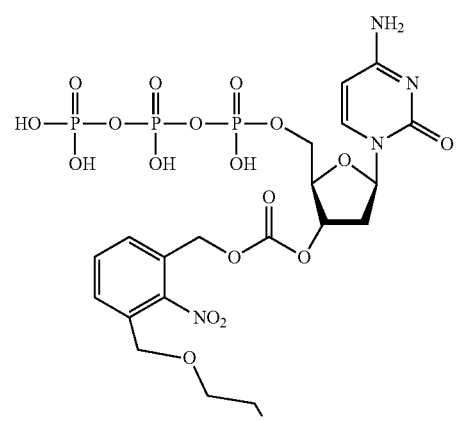

-continued
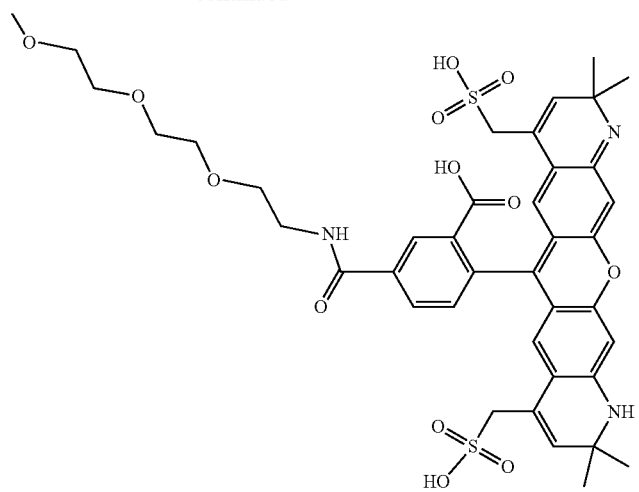
3′O dCTP
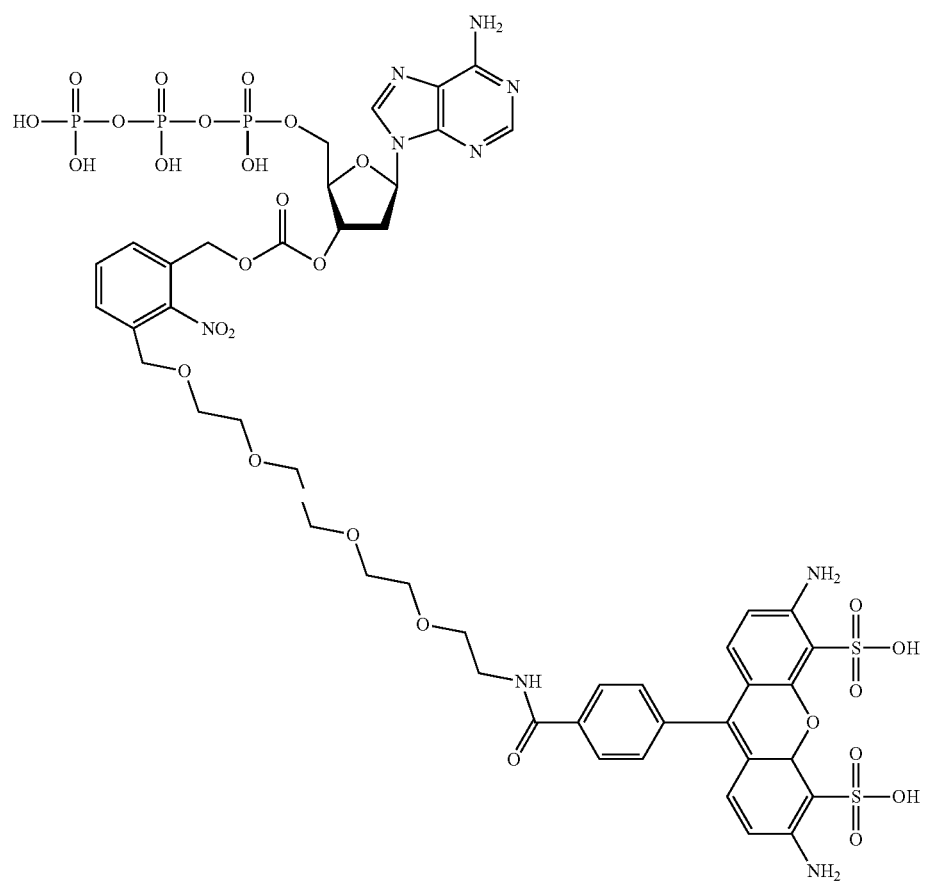
3′O dATP

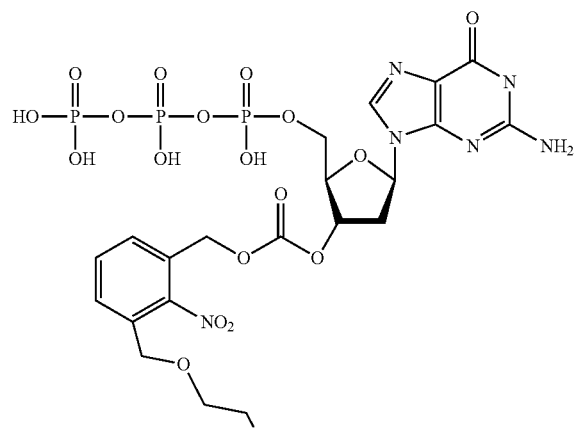
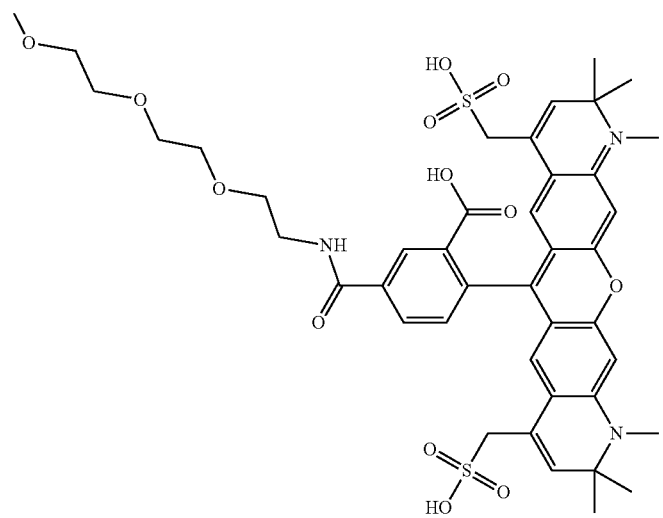
3' O dGTP
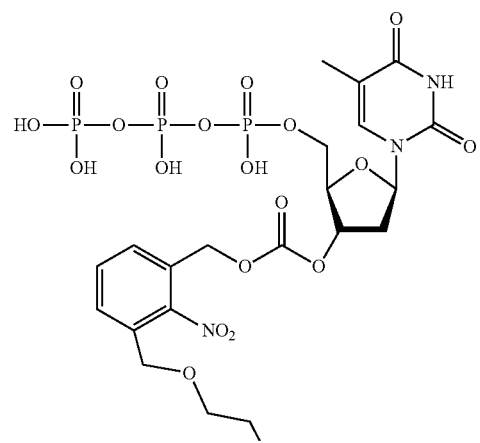

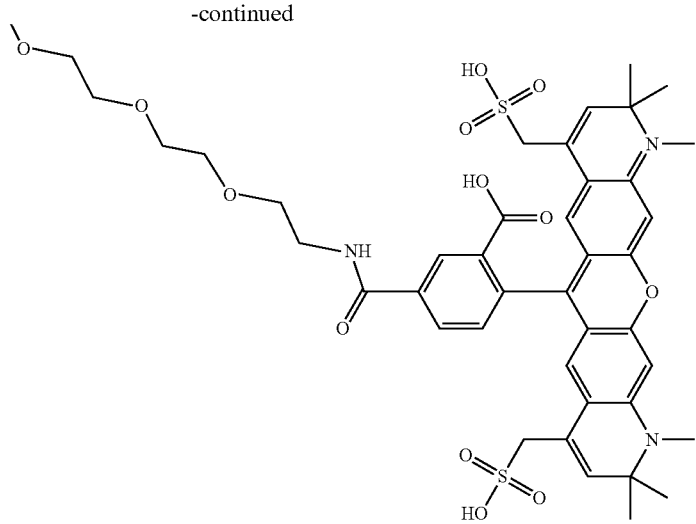
3'O dTTP
An exemplary synthesis procedure is provided as follows.
Synthesis of 3'O dTTP
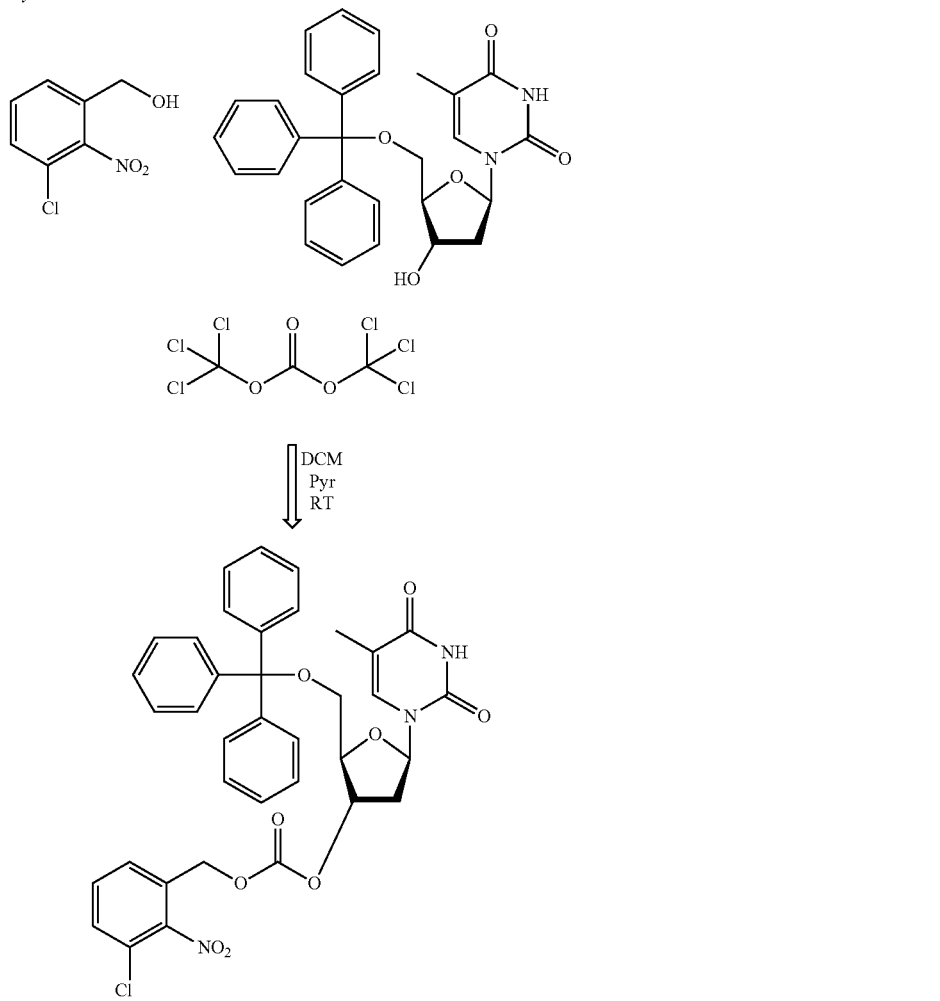

-continued
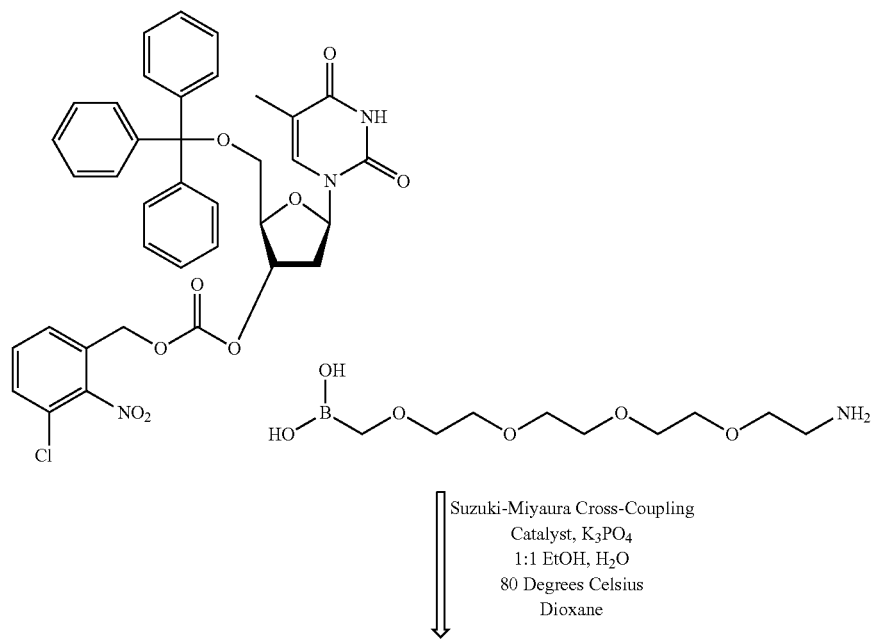
Suzuki-Miyaura Cross-Coupling
Catalyst, K₃PO₄
1:1 EtOH, H₂O
80 Degrees Celsius
Dioxane
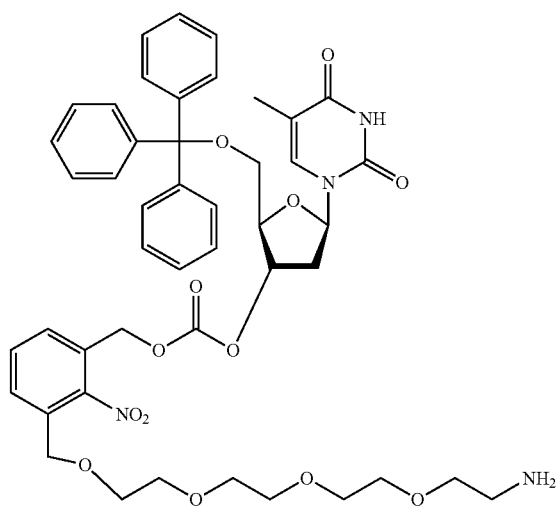
An Extremely Active and General Catalyst for Suzuki Coupling Reaction of Unreactive Aryl Chlorides
D.-H. Lee, M.-J. Jin, Org. Lett., 2011, 13, 252-255.

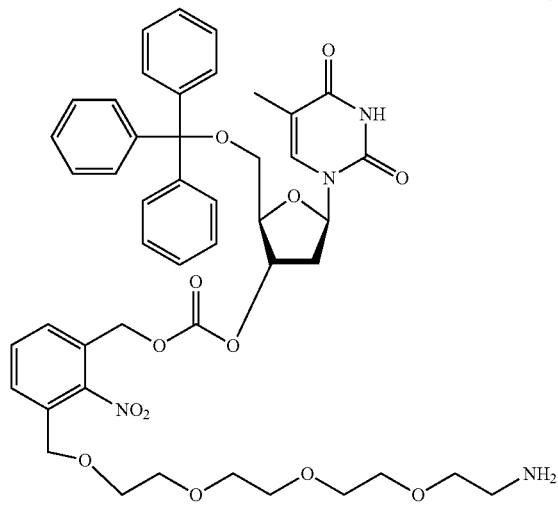
Detritylation
TEAA/AcOH
40 Degees Celsius
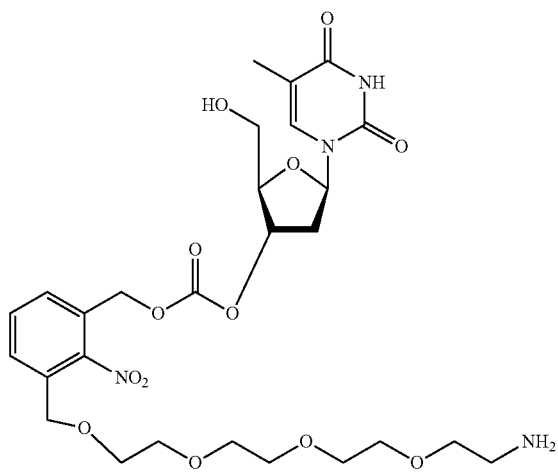
Salon, J., Zhang, B., & Huang, Z. (2011). Mild Detritylation of Nucleic Acid Hydroxyl Groups by Warming-up. Nucleosides, Nucleotides & Nucleic Acids, 30(4), 271-279.
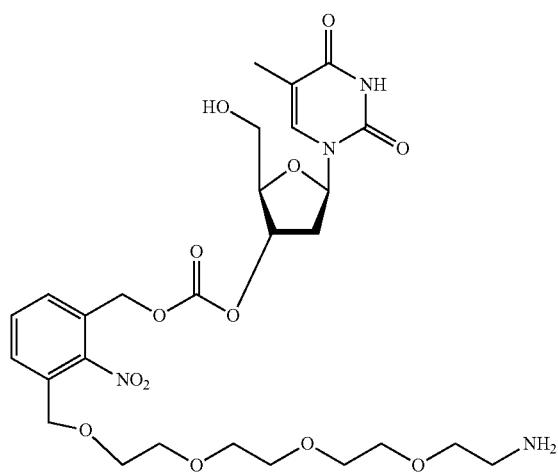

-continued
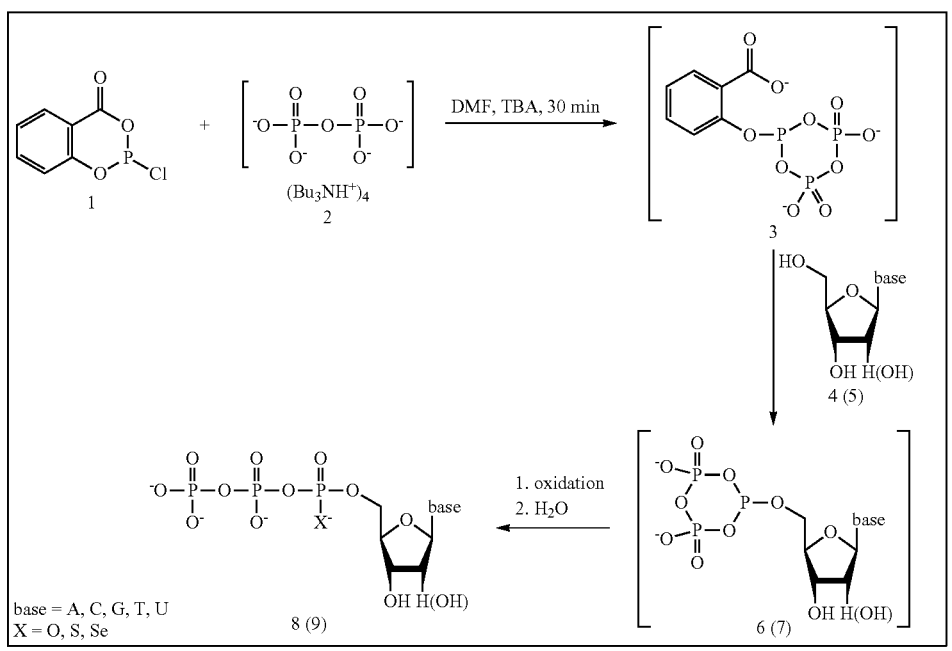
Caton-Williams, J., Hoxhaj, R., Fiaz, B. & Huang, Z. Use of a novel 5′-regioselective phosphitylating reagent for one-pot synthesis of nucleoside 5′-triphosphates from unprotected nucleosides. Curr. Protoc. Nucleic Acid Chem. Chapter 1, Unit 1.30 (2013).
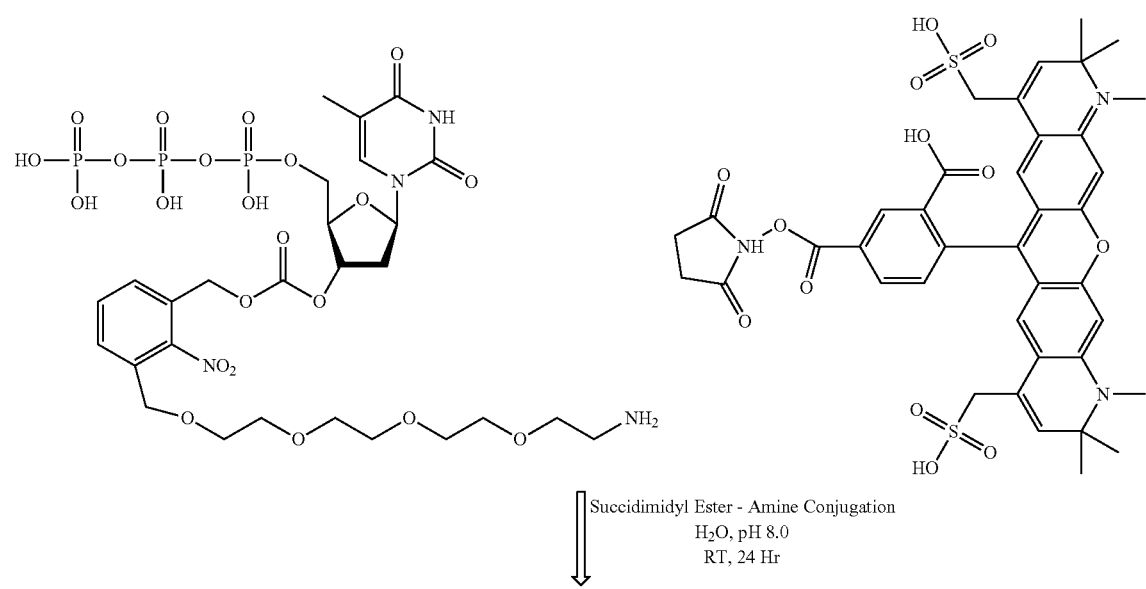
Succidimidyl Ester - Amine Conjugation
$H_2O$, pH 8.0
RT, 24 Hr -continued

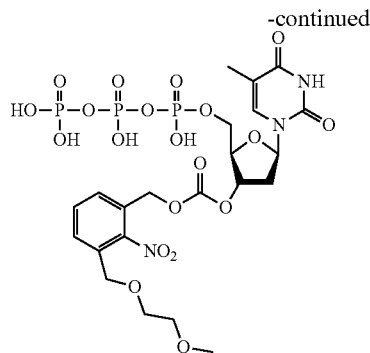
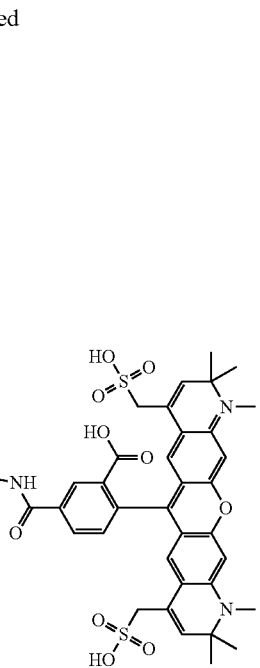

Polymerases

According to an alternate embodiment of the present invention, polymerases are used to build nucleic acid molecules representing information which is referred to herein as being recorded in the nucleic acid sequence or the nucleic acid is referred to herein as being storage media. Polymerases are enzymes that produce a nucleic acid sequence, for example, using DNA or RNA as a template. Polymerases that produce RNA polymers are known as RNA polymerases, while polymerases that produce DNA polymers are known as DNA polymerases. Polymerases that incorporate errors are known in the art and are referred to herein as an "error-prone polymerases". Template independent polymerases may be error prone polymerases. Using an error-prone polymerase allows the incorporation of specific bases at precise locations of the DNA molecule. Error-prone polymerases will either accept a non-standard base, such as a reversible chain terminating base, or will incorporate a different nucleotide, such as a natural or unmodified nucleotide that is selectively given to it as it tries to copy a template. Template-independent polymerases such as terminal deoxynucleotidyl transferase (TdT), also known as DNA nucleotidylexotransferase (DNTT) or terminal transferase create nucleic acid strands by catalyzing the addition of nucleotides to the 3' terminus of a DNA molecule without a template. The preferred substrate of TdT is a 3'-overhang, but it can also add nucleotides to blunt or recessed 3' ends. Cobalt is a cofactor, however the enzyme catalyzes reaction upon Mg and Mn administration in vitro. Nucleic acid initiators may be 4 or 5 nucleotides or longer and may be single stranded or double stranded. Double stranded initiators may have a 3' overhang or they may be blunt ended or they may have a 3' recessed end.

TdT, like all DNA polymerases, also requires divalent metal ions for catalysis. However, TdT is unique in its ability to use a variety of divalent cations such as Co2+, Mn2+, Zn2+ and Mg2+. In general, the extension rate of the primer p(dA)n (where n is the chain length from 4 through 50) with dATP in the presence of divalent metal ions is ranked in the following order: Mg2+>Zn2+>Co2+>Mn2+. In addition, each metal ion has different effects on the kinetics of nucleotide incorporation. For example, Mg2+ facilitates the preferential utilization of dGTP and dATP whereas Co2+ increases the catalytic polymerization efficiency of the pyrimidines, dCTP and dTTP. Zn2+ behaves as a unique positive effector for TdT since reaction rates with Mg2+ are stimulated by the addition of micromolar quantities of Zn2+. This enhancement may reflect the ability of Zn2+ to induce conformational changes in TdT that yields higher catalytic efficiencies. Polymerization rates are lower in the presence of Mn2+ compared to Mg2+, suggesting that Mn2+ does not support the reaction as efficiently as Mg2+. Further description of TdT is provided in *Biochim Biophys Acta., May* 2010; 1804(5): 1151-1166 hereby incorporated by reference in its entirety. In addition, one may replace Mg2+, Zn2+, Co2+, or Mn2+ in the nucleotide pulse with other cations designed modulate nucleotide attachment. For example, if the nucleotide pulse replaces Mg++ with other cation(s), such as Na+, K+, Rb+, Be++, Ca++, or Sr++, then the nucleotide can bind but not incorporate, thereby regulating whether the nucleotide will incorporate or not. Then a pulse of (optional) pre-wash without nucleotide or Mg++ can be provided or then Mg++ buffer without nucleotide can be provided.

By limiting nucleotides available to the polymerase, the incorporation of specific nucleic acids into the polymer can be regulated. Thus, these polymerases are capable of incorporating nucleotides independent of the template sequence and are therefore beneficial for creating nucleic acid sequences de novo. The combination of an error-prone polymerase and a primer sequence serves as a writing mechanism for imparting information into a nucleic acid sequence.

By limiting nucleotides available to a template independent polymerase, the addition of a nucleotide to an initiator sequence or an existing nucleotide or oligonucleotide can be regulated to produce an oligonucleotide by extension. Thus, these polymerases are capable of incorporating nucleotides without a template sequence and are therefore beneficial for creating nucleic acid sequences de novo.

The eta-polymerase (Matsuda et al. (2000) Nature 404 (6781):1011-1013) is an example of a polymerase having a high mutation rate (10%) and high tolerance for 3' mismatch in the presence of all 4 dNTPs and probably even higher if limited to one or two dNTPs. Hence, the eta-polymerase is a de novo recorder of nucleic acid information similar to terminal deoxynucleotidyl transferase (TdT) but with the advantage that the product produced by this polymerase is continuously double-stranded. Double stranded DNA has less sticky secondary structure and has a more predictable secondary structure than single stranded DNA. Furthermore, double stranded DNA serves as a good support for polymerases and/or DNA-binding-protein tethers.

According to certain aspects, a template dependent or template semi-dependent error prone polymerase can be used. According to certain embodiments, a template dependent polymerase may be used which may become error prone. According to certain embodiments, a template independent RNA polymerase can be used. Where a template dependent or template semi-dependent polymerase is used, any combination of templates with universal bases can be used which encourage acceptance of many nucleotide types. In addition, error tolerant cations such as $Mn^+$ can be used. Further, the present disclosure contemplates the use of error-tolerant polymerase mutants. See Berger et al., Universal Bases for Hybridization, Replication and Chain Termination, Nucleic Acids Research 2000, Aug. 1, 28(15) pp. 2911-2914 hereby incorporated by reference.

Nucleic acids that have been synthesized on the surface of a support may be removed, such as by a cleavable linker or linkers known to those of skill in the art. The nucleic acids may be positioned on a different substrate, such as at a higher density than the manufacturing density, or on a different substrate that is to serve as the storage medium. Also, additional layers of substrates may be added which serve as new substrates for additional nucleic acid synthesis. Accordingly, methods are provided to make a high density nucleic acid storage device by generating a plurality of oligonucleotides on a first substrate, removing the plurality of oligonucleotides from the first substrate and attaching them to a second substrate in a random or ordered manner and with a desired density.

Modulation Schemes for DNA Polymerization

A general method for synthesis of a nucleic acid, i.e. DNA, sequence includes control of the enzymatic extension by modulation of the ssDNA-enzyme-nucleotide complex composition. Extension modulation can be binary, i.e. either the system allows for extension or it does not, through a variety environmental variables that control extension activity. The factors governing whether extension can proceed must be satisfied. For extension to proceed, all state variables must evaluate as true. Any invertible transformation of the extension state from T→F following extension, then from F→T prior to extension enables discrete single nucleotide extension of an ssDNA sequence.

The state of the catalytic ions can be used to modulate single strand (ss) DNA synthesis. For example, the redox state of the catalytic ion can be altered. The catalytic ion can be photochemically or electrochemically reduced or oxidized rapidly to modulate extension. Extension requires a two metal divalent ion mechanism to stabilize the phosphodiester intermediates. Divalent ions may be reduced or oxidized by electrodes independently controlled in an array. The spatial presence of the catalytic ions can be altered. Two catalytic transition metal ions are required for catalytic activity. The ion can be rapidly transported away from an enzyme fixed in space by electrophoresis, or electroosmosis. The identity of the catalytic ion can be altered. The ion can be Mn, Zn, Mg, or Co. Ions such as Cu can competitively inhibit ion activity. EDTA and ion chelating agents can also inhibit enzyme activity.

The state of the template independent polymerase ions can be used to modulate single strand (ss) DNA synthesis by switching between an enzymatically active conformation and an enzymatically inactive conformation. Template independent DNA polymerases such as TdT can be reversibly modified by manipulation of the flexible loop region into a template dependent state. One can install azobenzene unnatural amino acids to a flexible loop region proximal to the active site of the enzyme. This allows photoreversible conformational changes to inhibit extension. Enzymes can be irreversibly denatured in strong electric fields. At other electric field Intensities, the choice of electric field magnitudes the denaturation is reversible. The enzyme may also be irreversibly denatured by heating, therefore heating elements may be used to modulate extension in an array. The Enzyme can be denatured by addition of chaotropic salts, and renatured by removal of chaotropic salts can be achieved by methods such as electrophoresis, dialysis, or electrodialysis.

The presence of the template independent polymerase ions can be used to modulate single strand (ss) DNA synthesis. For a ssDNA primer fixed in space, Template independent DNA polymerases can be spatially modulated in electric fields to move to or away from the primer. The method for unlabeled enzymes can be electrophoresis, dielectrophoresis. For magnetic bead attached enzymes, the method can use a magnetic field to control locality of the enzyme with reference to the primer. Locality of the enzyme may be modulated by washing the enzyme away in solution.

Suitable sidechain protonation of the active site can be used to modulate single strand (ss) DNA synthesis. The pH of the environment dictates the time averaged protonation state of side chains critical in intermediate stabilization. Localized pH changes by electrochemical or photochemical acid generators can reversibly modulate the activity of TdT.

The state of the ssDNA can be used to modulate single strand (ss) DNA synthesis. The spatial presence of the ssDNA sequence to be altered. Although generally assumed to be fixed in space, a primer can be free floating and modulated in space under an electric field by previously discussed techniques. The ssDNA strand may also be attached to bead magnetic or dielectric, where the control modality is magnetic field, or Dielectrophoresis, Optical Trapping respectively. For enzymatic extension, a free 3'OH must be present. The 3'OH might be protected as an ester or ether which is transformed by some cleavage event to the catalytically active 3'OH. Assuming the presence of the 3' OH, it must be accessible to the enzyme for extension. Large functional groups around the 3' OH or on the nucleobase can inhibit extension of the primer. These functional groups may be cleaved off in a separate reaction to return the capacity for extension of the ssDNA. Large cleavable modifications of the nucleobase can also prevent subsequent Polyphosphate coordination suitable for extension. If the Nucleobase modification is cleaved extension can proceed.

The state of the incoming dNTP can be used to modulate single strand (ss) DNA synthesis. For extension to proceed, the dNTP must be spatially present and in complex with the active site of TdT. This locality may be modulated by washing the dNTP away in solution. Alternatively, the dNTPs may be electrophoresed away, or transported by Electroosmostic flow. For formation of the phosphodiester bond, the polyphosphate must be sterically accessible so as to complex with the catalytic metal ion complex with a proper coordination geometry. If other components in the complex sterically hinder this interaction the reaction cannot proceed.

Supports and Attachment

In certain exemplary embodiments, one or more oligonucleotide sequences described herein are immobilized on a support (e.g., a solid and/or semi-solid support). In certain aspects, an oligonucleotide sequence can be attached to a support using one or more of the phosphoramidite linkers described herein. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. Supports of the present invention can be any shape, size, or geometry as desired. For example, the support may be square, rectangular, round, flat, planar, circular, tubular, spherical, and the like. When using a support that is substantially planar, the support may be physically separated into regions, for example, with trenches, grooves, wells, or chemical barriers (e.g., hydrophobic coatings, etc.). Supports may be made from glass (silicon dioxide), metal, ceramic, polymer or other materials known to those of skill in the art. Supports may be a solid, semi-solid, elastomer or gel. In certain exemplary embodiments, a support is a microarray. As used herein, the term "microarray" refers in one embodiment to a type of array that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate create a substantially planar surface. Spatially defined sites may additionally be "addressable" in that its location and the identity of the immobilized probe at that location are known or determinable.

The solid supports can also include a semi-solid support such as a compressible matrix with both a solid and a liquid component, wherein the liquid occupies pores, spaces or other interstices between the solid matrix elements. Preferably, the semi-solid support materials include polyacrylamide, cellulose, poly dimethyl siloxane, polyamide (nylon) and cross-linked agarose, -dextran and -polyethylene glycol. Solid supports and semi-solid supports can be used together or independent of each other.

Supports can also include immobilizing media. Such immobilizing media that are of use according to the invention are physically stable and chemically inert under the conditions required for nucleic acid molecule deposition and amplification. A useful support matrix withstands the rapid changes in, and extremes of, temperature required for PCR. The support material permits enzymatic nucleic acid synthesis. If it is unknown whether a given substance will do so, it is tested empirically prior to any attempt at production of a set of arrays according to the invention. According to one embodiment of the present invention, the support structure comprises a semi-solid (i.e., gelatinous) lattice or matrix, wherein the interstices or pores between lattice or matrix elements are filled with an aqueous or other liquid medium; typical pore (or 'sieve') sizes are in the range of 100 µm to 5 nm. Larger spaces between matrix elements are within tolerance limits, but the potential for diffusion of amplified products prior to their immobilization is increased. The semi-solid support is compressible. The support is prepared such that it is planar, or effectively so, for the purposes of printing. For example, an effectively planar support might be cylindrical, such that the nucleic acids of the array are distributed over its outer surface in order to contact other supports, which are either planar or cylindrical, by rolling one over the other. Lastly, a support material of use according to the invention permits immobilizing (covalent linking) of nucleic acid features of an array to it by means known to those skilled in the art. Materials that satisfy these requirements comprise both organic and inorganic substances, and include, but are not limited to, polyacrylamide, cellulose and polyamide (nylon), as well as cross-linked agarose, dextran or polyethylene glycol.

One embodiment is directed to a thin polyacrylamide gel on a glass support, such as a plate, slide or chip. A polyacrylamide sheet of this type is synthesized as follows. Acrylamide and bis-acrylamide are mixed in a ratio that is designed to yield the degree of crosslinking between individual polymer strands (for example, a ratio of 38:2 is typical of sequencing gels) that results in the desired pore size when the overall percentage of the mixture used in the gel is adjusted to give the polyacrylamide sheet its required tensile properties. Polyacrylamide gel casting methods are well known in the art (see Sambrook et al., 1989, *Molecular Cloning. A Laboratory Manual,* 2nd Edition, Cold Spring Harbor Laboratory Press, Cold Spring Harbor, N.Y., incorporated herein in its entirety by reference), and one of skill has no difficulty in making such adjustments.

The gel sheet is cast between two rigid surfaces, at least one of which is the glass to which it will remain attached after removal of the other. The casting surface that is to be removed after polymerization is complete is coated with a lubricant that will not inhibit gel polymerization; for this purpose, silane is commonly employed. A layer of silane is spread upon the surface under a fume hood and allowed to stand until nearly dry. Excess silane is then removed (wiped or, in the case of small objects, rinsed extensively) with ethanol. The glass surface which will remain in association with the gel sheet is treated with γ-methacryloxypropyltrimethoxysilane (Cat. No. M6514, Sigma; St. Louis, Mo.), often referred to as 'crosslink silane', prior to casting. The glass surface that will contact the gel is triply-coated with this agent. Each treatment of an area equal to 1200 cm$^2$ requires 125 µl of crosslink silane in 25 ml of ethanol Immediately before this solution is spread over the glass surface, it is combined with a mixture of 750 µl water and 75 µl glacial acetic acid and shaken vigorously. The ethanol solvent is allowed to evaporate between coatings (about 5 minutes under a fume hood) and, after the last coat has dried, excess crosslink silane is removed as completely as possible via extensive ethanol washes in order to prevent 'sandwiching' of the other support plate onto the gel. The plates are then assembled and the gel cast as desired.

The only operative constraint that determines the size of a gel that is of use according to the invention is the physical ability of one of skill in the art to cast such a gel. The casting of gels of up to one meter in length is, while cumbersome, a procedure well known to workers skilled in nucleic acid sequencing technology. A larger gel, if produced, is also of use according to the invention. An extremely small gel is cut from a larger whole after polymerization is complete.

Note that at least one procedure for casting a polyacrylamide gel with bioactive substances, such as enzymes, entrapped within its matrix is known in the art (O'Driscoll, 1976, *Methods Enzymol.*, 44: 169-183, incorporated herein in its entirety by reference). A similar protocol, using photo-crosslinkable polyethylene glycol resins, that permit entrapment of living cells in a gel matrix has also been documented (Nojima and Yamada, 1987, *Methods Enzymol.*, 136: 380-394, incorporated herein in its entirety by reference). Such methods are of use according to the invention. As mentioned below, whole cells are typically cast into agarose for the purpose of delivering intact chromosomal DNA into a matrix suitable for pulsed-field gel electrophoresis or to serve as a "lawn" of host cells that will support bacteriophage growth prior to the lifting of plaques according to the method of Benton and Davis (see Maniatis et al., 1982, *Molecular Cloning: A Laboratory Manual*, Cold Spring Harbor Laboratory Press, Cold Spring Harbor, N.Y., incorporated herein in its entirety by reference). In short, electrophoresis-grade agarose (e.g., Ultrapure; Life Technologies/Gibco-BRL) is dissolved in a physiological (isotonic) buffer and allowed to equilibrate to a temperature of 50° C. to 52° C. in a tube, bottle or flask. Cells are then added to the agarose and mixed thoroughly, but rapidly (if in a bottle or tube, by capping and inversion, if in a flask, by swirling), before the mixture is decanted or pipetted into a gel tray. If low-melting point agarose is used, it may be brought to a much lower temperature (down to approximately room temperature, depending upon the concentration of the agarose) prior to the addition of cells. This is desirable for some cell types; however, if electrophoresis is to follow cell lysis prior to covalent attachment of the molecules of the resultant nucleic acid pool to the support, it is performed under refrigeration, such as in a 4° C. to 10° C. 'cold' room.

Oligonucleotides immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. In certain exemplary embodiments, probes are immobilized via one or more cleavable linkers. The density of non-overlapping regions containing nucleic acids in a microarray is typically greater than 100 per $cm^2$, and more typically, greater than 1000 per $cm^2$. Microarray technology relating to nucleic acid probes is reviewed in the following exemplary references: Schena, Editor, Microarrays: A Practical Approach (IRL Press, Oxford, 2000); Southern, Current Opin. Chem. Biol., 2: 404-410 (1998); Nature Genetics Supplement, 21:1-60 (1999); and Fodor et al, U.S. Pat. Nos. 5,424,186; 5,445,934; and 5,744,305.

Methods of immobilizing oligonucleotides to a support are known in the art (beads: Dressman et al. (2003) Proc. Natl. Acad. Sci. USA 100:8817, Brenner et al. (2000) Nat. Biotech. 18:630, Albretsen et al. (1990) Anal. Biochem. 189:40, and Lang et al. Nucleic Acids Res. (1988) 16:10861; nitrocellulose: Ranki et al. (1983) Gene 21:77; cellulose: Goldkorn (1986) Nucleic Acids Res. 14:9171; polystyrene: Ruth et al. (1987) Conference of Therapeutic and Diagnostic Applications of Synthetic Nucleic Acids, Cambridge U.K.; teflon-acrylamide: Duncan et al. (1988) Anal. Biochem. 169:104; polypropylene: Polsky-Cynkin et al. (1985) Clin. Chem. 31:1438; nylon: Van Ness et al. (1991) Nucleic Acids Res. 19:3345; agarose: Polsky-Cynkin et al., Clin. Chem. (1985) 31:1438; and sephacryl: Langdale et al. (1985) Gene 36:201; latex: Wolf et al. (1987) Nucleic Acids Res. 15:2911). Supports may be coated with attachment chemistry or polymers, such as amino-silane, NHS-esters, click chemistry, polylysine, etc., to bind a nucleic acid to the support.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994.

According to certain aspects, affixing or immobilizing nucleic acid molecules to the substrate is performed using a covalent linker that is selected from the group that includes oxidized 3-methyl uridine, an acrylyl group and hexaethylene glycol. In addition to the attachment of linker sequences to the molecules of the pool for use in directional attachment to the support, a restriction site or regulatory element (such as a promoter element, cap site or translational termination signal), is, if desired, joined with the members of the pool. Linkers can also be designed with chemically reactive segments which are optionally cleavable with agents such as enzymes, light, heat, pH buffers, and redox reagents. Such linkers can be employed to pre-fabricate an in situ solid-phase inactive reservoir of a different solution-phase primer for each discrete feature. Upon linker cleavage, the primer would be released into solution for PCR, perhaps by using the heat from the thermocycling process as the trigger.

It is also contemplated that affixing of nucleic acid molecules to the support is performed via hybridization of the members of the pool to nucleic acid molecules that are covalently bound to the support.

Immobilization of nucleic acid molecules to the support matrix according to the invention is accomplished by any of several procedures. Direct immobilizing via the use of 3'-terminal tags bearing chemical groups suitable for covalent linkage to the support, hybridization of single-stranded molecules of the pool of nucleic acid molecules to oligonucleotide primers already bound to the support, or the spreading of the nucleic acid molecules on the support accompanied by the introduction of primers, added either before or after plating, that may be covalently linked to the support, may be performed. Where pre-immobilized primers are used, they are designed to capture a broad spectrum of sequence motifs (for example, all possible multimers of a given chain length, e.g., hexamers), nucleic acids with homology to a specific sequence or nucleic acids containing variations on a particular sequence motif. Alternatively, the primers encompass a synthetic molecular feature common to all members of the pool of nucleic acid molecules, such as a linker sequence.

Two means of crosslinking a nucleic acid molecule to a polyacrylamide gel sheet will be discussed in some detail. The first (provided by Khrapko et al., 1996, U.S. Pat. No. 5,552,270) involves the 3' capping of nucleic acid molecules with 3-methyl uridine. Using this method, the nucleic acid molecules of the libraries of the present invention are prepared so as to include this modified base at their 3' ends. In the cited protocol, an 8% polyacrylamide gel (30:1, acrylamide: bis-acrylamide) sheet 30 μm in thickness is cast and then exposed to 50% hydrazine at room temperature for 1 hour. Such a gel is also of use according to the present invention. The matrix is then air dried to the extent that it will absorb a solution containing nucleic acid molecules, as described below. Nucleic acid molecules containing 3-methyl uridine at their 3' ends are oxidized with 1 mM sodium periodate (NaIO$_4$) for 10 minutes to 1 hour at room temperature, precipitated with 8 to 10 volumes of 2% LiClO$_4$ in acetone and dissolved in water at a concentration of 10 pmol/μl. This concentration is adjusted so that when the nucleic acid molecules are spread upon the support in a volume that covers its surface evenly and is efficiently (i.e., completely) absorbed by it, the density of nucleic acid molecules of the array falls within the range discussed above. The nucleic acid molecules are spread over the gel surface and the plates are placed in a humidified chamber for 4 hours. They are then dried for 0.5 hour at room temperature and washed in a buffer that is appropriate to their subsequent use. Alternatively, the gels are rinsed in water, re-dried and stored at −20° C. until needed. It is thought that the overall yield of nucleic acid that is bound to the gel is 80% and that of these molecules, 98% are specifically linked through their oxidized 3' groups.

A second crosslinking moiety that is of use in attaching nucleic acid molecules covalently to a polyacrylamide sheet is a 5' acrylyl group, which is attached to the primers. Oligonucleotide primers bearing such a modified base at their 5' ends may be used according to the invention. In particular, such oligonucleotides are cast directly into the gel, such that the acrylyl group becomes an integral, covalently bonded part of the polymerizing matrix. The 3' end of the primer remains unbound, so that it is free to interact with, and hybridize to, a nucleic acid molecule of the pool and prime its enzymatic second-strand synthesis.

Alternatively, hexaethylene glycol is used to covalently link nucleic acid molecules to nylon or other support matrices (Adams and Kron, 1994, U.S. Pat. No. 5,641,658). In addition, nucleic acid molecules are crosslinked to nylon via irradiation with ultraviolet light. While the length of time for which a support is irradiated as well as the optimal distance from the ultraviolet source is calibrated with each instrument used due to variations in wavelength and transmission strength, at least one irradiation device designed specifically for crosslinking of nucleic acid molecules to hybridization membranes is commercially available (Stratalinker, Stratagene). It should be noted that in the process of crosslinking via irradiation, limited nicking of nucleic acid strands occurs. The amount of nicking is generally negligible, however, under conditions such as those used in hybridization procedures. In some instances, however, the method of ultraviolet crosslinking of nucleic acid molecules will be unsuitable due to nicking. Attachment of nucleic acid molecules to the support at positions that are neither 5'- nor 3'-terminal also occurs, but it should be noted that the potential for utility of an array so crosslinked is largely uncompromised, as such crosslinking does not inhibit hybridization of oligonucleotide primers to the immobilized molecule where it is bonded to the support.

Supports described herein may have one or more optically addressable virtual electrodes associated therewith such that an anion toroidal vortex can be created at a reaction site on the supports described herein.

Reagent Delivery Systems

According to certain aspects, reagents and washes are delivered that the reactants are present at a desired location for a desired period of time to, for example, covalently attached dNTP to an initiator sequence or an existing nucleotide attached at the desired location. A selected nucleotide reagent liquid is pulsed or flowed or deposited at the reaction site where reaction takes place and then may be optionally followed by delivery of a buffer or wash that does not include the nucleotide. Suitable delivery systems include fluidics systems, microfluidics systems, syringe systems, ink jet systems, pipette systems and other fluid delivery systems known to those of skill in the art. Various flow cell embodiments or flow channel embodiments or microfluidic channel embodiments are envisioned which can deliver separate reagents or a mixture of reagents or washes using pumps or electrodes or other methods known to those of skill in the art of moving fluids through channels or microfluidic channels through one or more channels to a reaction region or vessel where the surface of the substrate is positioned so that the reagents can contact the desired location where a nucleotide is to be added.

According to another embodiment, a microfluidic device is provided with one or more reservoirs which include one or more reagents which are then transferred via microchannels to a reaction zone where the reagents are mixed and the reaction occurs. Such microfluidic devices and the methods of moving fluid reagents through such microfluidic devices are known to those of skill in the art.

Immobilized nucleic acid molecules may, if desired, be produced using a device (e.g., any commercially-available inkjet printer, which may be used in substantially unmodified form) which sprays a focused burst of reagent-containing solution onto a support (see Castellino (1997) *Genome Res.* 7:943-976, incorporated herein in its entirety by reference). Such a method is currently in practice at Incyte Pharmaceuticals and Rosetta Biosystems, Inc., the latter of which employs "minimally modified Epson inkjet cartridges" (Epson America, Inc.; Torrance, Calif.). The method of inkjet deposition depends upon the piezoelectric effect, whereby a narrow tube containing a liquid of interest (in this case, oligonucleotide synthesis reagents) is encircled by an adapter. An electric charge sent across the adapter causes the adapter to expand at a different rate than the tube, and forces a small drop of liquid reagents from the tube onto a coated slide or other support.

Reagents can be deposited onto a discrete region of the support, such that each region forms a feature of the array. The feature is capable of generating an anion toroidal vortex as described herein. The desired nucleic acid sequence can be synthesized drop-by-drop at each position, as is true for other methods known in the art. If the angle of dispersion of reagents is narrow, it is possible to create an array comprising many features. Alternatively, if the spraying device is more broadly focused, such that it disperses nucleic acid synthesis reagents in a wider angle, as much as an entire support is covered each time, and an array is produced in which each member has the same sequence (i.e., the array has only a single feature).

There are contemplated different distributions for the time for binding a nucleotide precursor (dNTP/rNTP/rNDP) and time spent in making the covalent bond with the growing primer 3' end. An array-based, flow-cell technique is used, similar to standard synthesis and sequencing procedures. Starting TdT primers are bonded to flat silicon dioxide (or 10 micron thick polymer layer) at known locations which are capable of generating an anion toroidal vortex as described herein. Locations for creating oligonucleotides can range in number between 1,000 and 5,000,000.

Retrieval of Verified Polynucleotides from the Array

The disclosure provides the use of orthogonal PCR barcodes that are synthesized or otherwise provided on initiator strands which are attached to the substrate, which can be an array, prior to synthesis of the target sequence. These orthogonal per priming sites facilitate addressable amplification and recovery of individual molecules from the array after synthesis as is known in the art. All sequences in the array maintain a common reverse primer, and only those with perfect sequences are amplified from the array. Synthesized Target sequences may be as long as 10 kilobases. An exemplary DNA sequence arrangement is shown below. Orthogonal PCR barcode—Type IIs site—Target sequence—Type IIs site—Common reverse.

REFERENCES

The following references are identified as describing various features, methods, reagents etc. useful in the practice of the embodiments disclosed herein. Each reference is hereby incorporated by reference in its entirety.

1. Kosuri, S. & Church, G. M. Large-scale de novo DNA synthesis: technologies and applications. *Nat. Methods* 11, 499-507 (2014).
2. Beaucage, S. L. & Caruthers, M. H. Deoxynucleoside phosphoramidites—A new class of key intermediates for deoxypolynucleotide synthesis. *Tetrahedron Lett.* 22, 1859-1862 (1981).
3. Septak, M. Kinetic studies on depurination and detritylation of CPG-bound intermediates during oligonucleotide synthesis. *Nucleic Acids Res.* 24, 3053-3058 (1996).
4. LeProust, E. M. et al. Synthesis of high-quality libraries of long (150mer) oligonucleotides by a novel depurination controlled process. *Nucleic Acids Res.* 38, 2522-40 (2010).
5. Klán, P. et al. Photoremovable protecting groups in chemistry and biology: reaction mechanisms and efficacy. *Chem. Rev.* 113, 119-91 (2013).
6. Pirrung, M. C., Dore, T. M., Zhu, Y. & Rana, V. S. Sensitized two-photon photochemical deprotection. *Chem. Commun.* (*Camb*). 46, 5313-5 (2010).

Other Embodiments

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference in their entirety for all purposes to the same extent as if each individual publication or patent application were specifically and individually indicated to be so incorporated by reference.

The invention claimed is:

1. A method for making a polynucleotide comprising
   (a) delivering one or more reaction reagents including an error prone or template independent DNA polymerase, cations and a selected nucleotide to a reaction site including an initiator sequence having a terminal nucleotide for a time period and under conditions capable of covalently adding one or more of the selected nucleotide to the terminal nucleotide at the 3' end of the initiator such that the selected nucleotide becomes a terminal nucleotide, and
   (b) determining whether the selected nucleotide has been added to the terminal nucleotide, wherein if the selected nucleotide has not been added to the terminal nucleotide, then repeating step (a) until the selected nucleotide has been added, and
   (c) repeating steps (a) and (b) until the polynucleotide is formed,
   wherein the selected nucleotide has the following structure:

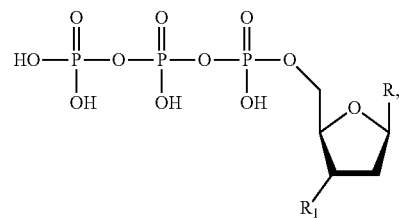

wherein R is standard base units, wherein $R_1$ is a cleavable linker, group or moiety of the following structure:

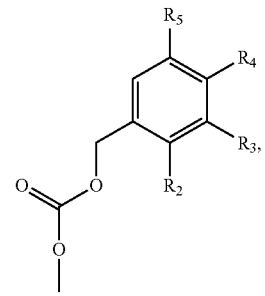

wherein $R_2$ is $NO_2$;

wherein $R_3$ is H or $R_7$;

wherein $R_4$ is H or $R_7$;

wherein $R_5$ is H or $R_6$;

wherein $R_6$ has the following structures:

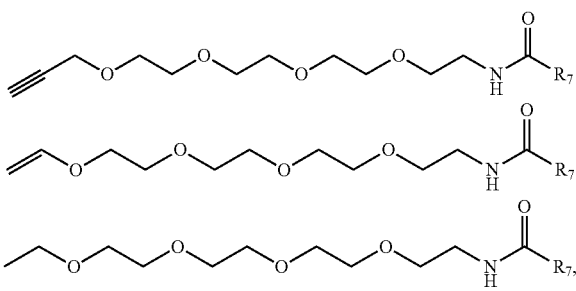

and
wherein R₇ has the following structures:

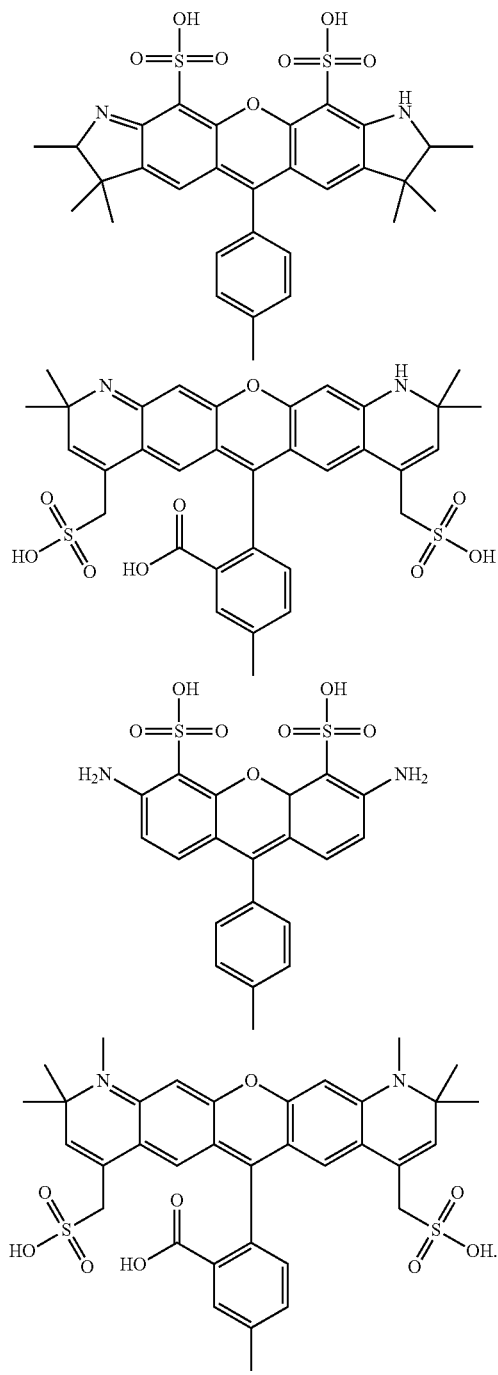

2. The method of claim 1 wherein a single selected nucleotide is covalently added.

3. The method of claim 1 wherein the error prone template independent DNA polymerase is terminal deoxynucleotide transferase.

4. The method of claim 1 including a plurality of reaction sites where steps (a) and (b) are performed.

5. The method of claim 1 wherein an incorrect nucleotide is added to the terminal nucleotide which is removed before repeating step (a) until the selected nucleotide has been added.

6. The method of claim 1 wherein whether the selected nucleotide has been added to the terminal nucleotide is determined by monitoring of a fluorescent signal.

7. The method of claim 1 wherein whether the selected nucleotide has been added to the terminal nucleotide is determined by monitoring photons, electrons, pH, or a chemical entity.

8. The method of claim 1 including a plurality of reaction sites where steps (a) and (b) are performed and wherein the plurality of reaction sites are monitored simultaneously or in parallel to determine whether the selected nucleotide has been added to the terminal nucleotide or whether an incorrect nucleotide has been added to the terminal nucleotide.

9. The method of claim 1 including a plurality of reaction sites where steps (a) and (b) are performed and wherein the plurality of reaction sites are monitored simultaneously or in parallel to determine whether the selected nucleotide has been added to the terminal nucleotide or whether an incorrect nucleotide has been added to the terminal nucleotide, and for one or more reaction sites where the selected nucleotide has not been added to the terminal nucleotide, repeating step (a) at each of the one or more reaction sites until the selected nucleotide has been added.

10. The method of claim 1 including a plurality of reaction sites where steps (a) and (b) are performed and wherein the plurality of reaction sites are monitored simultaneously or in parallel to determine whether the selected nucleotide has been added to the terminal nucleotide or whether an incorrect nucleotide has been added to the terminal nucleotide, and for one or more reaction sites where the incorrect nucleotide has been added to the terminal nucleotide, removing the incorrect nucleotide and repeating step (a) at each of the one or more reaction sites until the selected nucleotide has been added.

11. The method of claim 1 wherein the reaction reagents are removed from the reaction site by a volume of wash fluid.

12. The method of claim 1 wherein the one or more reaction reagents are delivered by microfluidics.

* * * * *